(12) United States Patent
Kitchings Weathers, Jr.

(10) Patent No.: US 6,419,490 B1
(45) Date of Patent: Jul. 16, 2002

(54) GROOVED INTRAOSSEOUS DENTAL DRILL BIT

(76) Inventor: Arthur Kitchings Weathers, Jr., 14 Hudson Rd., Griffin, GA (US) 30224

( * ) Notice: Subject to any disclaimer, the term of this patent is extended or adjusted under 35 U.S.C. 154(b) by 0 days.

(21) Appl. No.: 09/771,574

(22) Filed: Jan. 30, 2001

(51) Int. Cl.⁷ .................................................. A61C 3/02
(52) U.S. Cl. ........................................ 433/165; 606/80
(58) Field of Search ................................. 433/165, 166, 433/72, 80, 102, 116; 606/80, 180

(56) References Cited

U.S. PATENT DOCUMENTS

| | | | | |
|---|---|---|---|---|
| 5,173,050 A | * | 12/1992 | Dillon | 433/165 |
| 5,261,818 A | * | 11/1993 | Shaw | 433/165 |
| 5,762,639 A | * | 6/1998 | Gibbs | 604/272 |
| 5,779,708 A | * | 7/1998 | Wu | 606/80 |
| 5,941,706 A | * | 8/1999 | Ura | 433/165 |
| 6,135,769 A | * | 10/2000 | Kwan | 433/80 |

* cited by examiner

Primary Examiner—John J. Wilson
Assistant Examiner—Melba Bumgarner

(57) ABSTRACT

This application relates to a dental apparatus for the initial and subsequent guidance of hypodermic needles, or similar drug delivery devices into the cortical plate of human mandibular and maxillary bones. The invention comprises a solid drill bit bearing a channeling groove along the majority of the shaft. The groove is scalloped at its delivery end to flex the needle tip and deflect the tip out from the drill and into the desired tissue. Variations are described, with the preferred embodiment having the circumference of the drill bit reduced in girth for the length bearing the groove. This permits an inexpensive plastic covering which serves as a practical seal against bacteria. The seal is permeable to the needle's tip and closes back on itself after withdrawal of the needle.

15 Claims, 2 Drawing Sheets

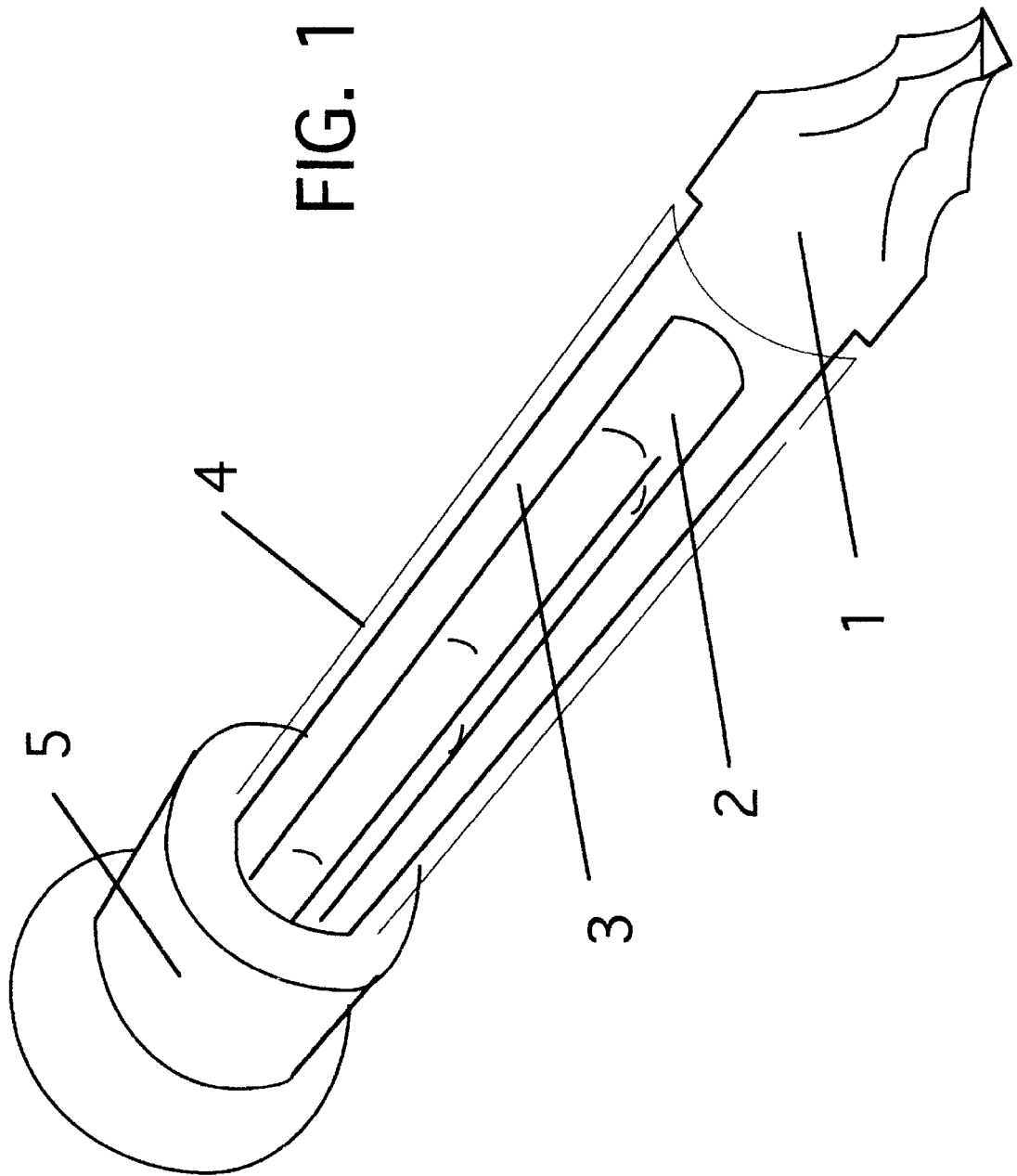

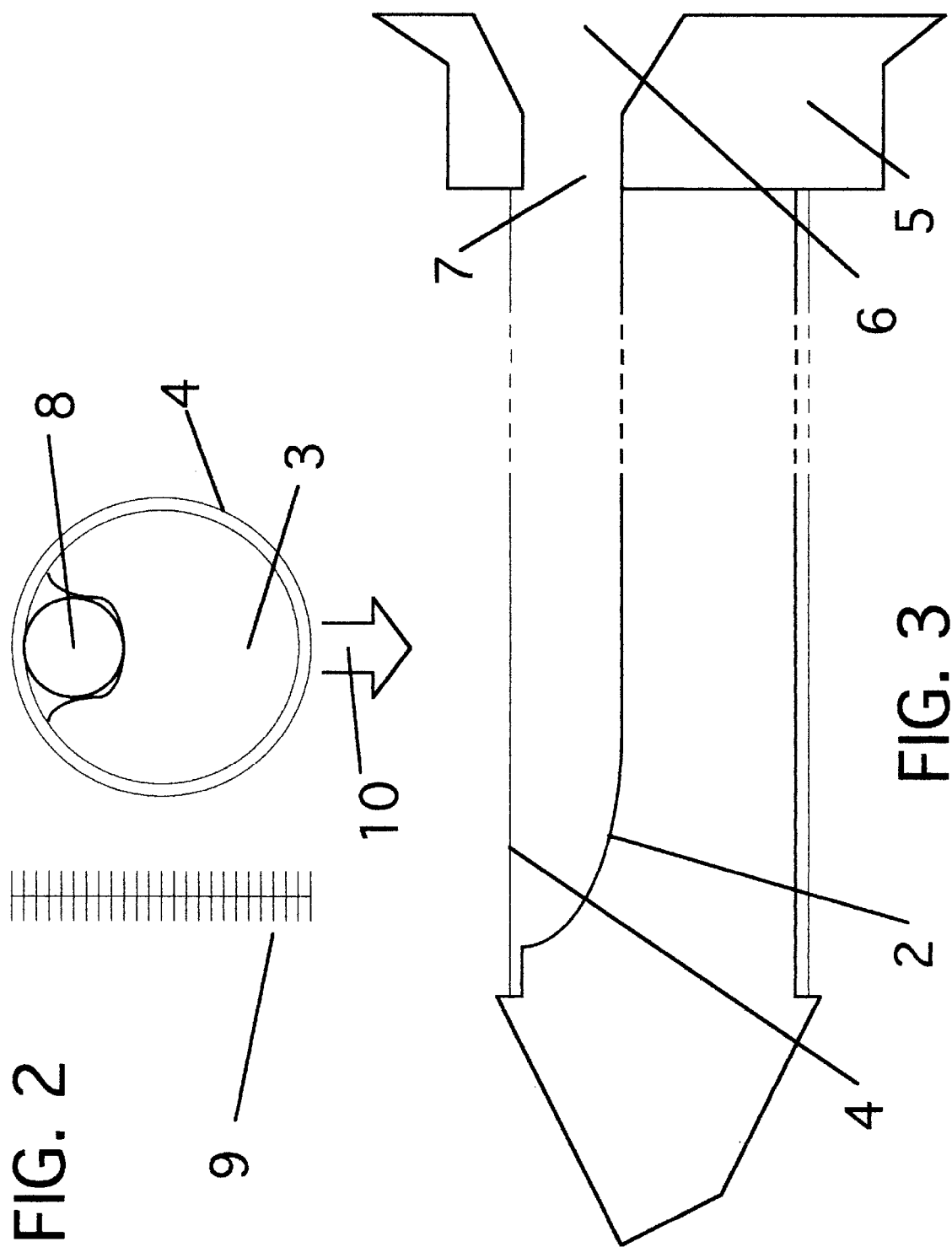

GROOVED INTRAOSSEOUS DENTAL DRILL BIT

This application relates to the field of medicine, and more specifically involves corrective measures to improve the success of intraosseous medication injections in Dentistry and related fields requiring anaesthesia.

DISCUSSION OF THE PRIOR ART

The art of deadening pain for the Dental industry was greatly improved by the discovery that smaller and more effective dosages of medication could be introduced beneath the cortical plate. Pivotally, U.S. Pat. No. 5,173,050 by Dillon in 1992 cited methods of and implements for drilling an initial perforation, thus allowing the dentist to remove the drill bit and re-enter the passageway with a hypodermic needle to deliver anaesthesia.

However, difficulties as taught by Dillon mainly involving failures of re-entry caused the industry to respond with two U.S. patents: U.S. Pat. No. 5,762,639 by Gibbs, and U.S. Pat. No. 5,779,708 by Wu, both describing methods to leave an intra-osseous hollow channel in place subsequent to drilling. This hollow channel served as a guidance system to allow re-entry for medicative purposes.

Adversely, the necessity of hollow guidance sleeves to themselves be drill bits increased the expense over Dillon and introduced dangers involving incidents of breakage of the tiny-diameter, hollow implements. The threat of the breakage and subsequent successful retrieval of all foreign objects from the patient is complicated by the presence as taught by Gibbs and Wu of other separate and intricate inner plugging stylets or rods. These latter implements strengthen the overall shaft and block the backflow of bone chips and other organic matter while drilling.

As a further response of the prior art, U.S. Pat. No. 6,135,769 by Kwan teaches a hollow drill bit with a side hole located a short distance up the drill shaft from the entry tip. The claimed advantage over Gibbs and Wu being no inner stylet is required, which reduces manufacturing costs. Also the step of removing the inner stylet after drilling is deleted.

A pertinent negative to the Kwan patent is the fact breakage of the drill bit is enhanced by two considerations:

1. Without the inner stylet of both Gibbs and Wu the overall strength of the Kwan drill bit is less in comparison.
2. The introduction of a hole through the hollow circular walls of the drill bit itself creates a hot-spot location that by its physical nature is weaker to torque stress than non-perforated positions along the drill bit. If breakage occurs, the likelihood is increased that the broken tip section will be unretrievable short of surgery. This is because the perforated section must advance to a functional depth such that it clears the inner wall of the hard bone to reach into the interior soft cancellous bone tissue.

Another pertinent negative for all patents utilizing channeled drills is the possible undesirable introduction of bacteria into the underlying tissues of the patient. The method of operation requires the drill to be left in the jawbone while dental work goes on, and thus in the process air or water mediums can introduce small but significant levels of living microbes.

OBJECTS AND ADVANTAGES

It is therefore accordingly an object of the present invention to provide a guidance channel through the cortical plate that does not employ a hollow drill bit, thus lessening the risk of breakage.

It is further accordingly an object of the present invention to provide a guidance channel through the cortical plate that lessens discomfort by offering the higher penetrative speed that a true solid drilling tip delivers.

It is further accordingly an object of the present invention to provide a guidance channel through the cortical plate of small manufacturing cost.

It is further accordingly an object of the present invention to provide a guidance channel through the cortical plate with a minimalized list of procedural steps for the Dentist.

It is further accordingly an object of the present invention to provide a guidance channel through the cortical plate that reduces the introduction of airborne or waterborne bacteria to the inner tissues while the drill is left in place.

These and many other objects and advantages will be readily apparent to one skilled in the art to which the invention pertains from a perusal of the claims and the following detailed description of preferred embodiments when read in conjunction with the appended drawings.

NATURE OF THE INVENTION

A solid drill bit can bear a functional groove or canyon along its shank reaching far enough down the overall length to allow the delivery of anaesthesia while the drill bit remains inside the bone. The groove is reduced in depth (scalloped) at its delivery end to flex the needle tip and deflect the tip out from the drill bit and into the desired tissue.

In the preferred embodiment a solid steel drill bit is turned at high speed on a lathe while a thin skin of steel is polished off with a diamond tipped abrasive. The resulting drill bit has a uniform circumference all along its shaft to a point near the drilling tip, where no polishing was done. In essence, the drill bit has a head and a long neck, with the neck reduced to a circumference still almost as large as the head itself.

Next a groove is cut along the length of the shaft sufficient to create a guidance channel for a typical drug delivery needle. The end of the groove near the tip is curved along the bottom, and this scalloping allows the depth of the groove to lessen. Before the drill bit is fabricated in an insertion injection molding machine with a plastic hub, a thin sleeve of tubular plastic such as polyethylene or polypropylene is fitted over the polished section of the drill bit. The circumference of the drill bit at the unpolished section is equal to or greater than the circumference of the polyethylene section, thus allowing the drill bit in use to bore and penetrate without stress to the polyethylene layer.

A dental handpiece is a drill that by design has a chuck to grasp either the hub or an adapter linked to the hub of a drill bit. The drill bit can then perforate the cortical plate and be detached from the handpiece. The subsequent removal of the handpiece leaves a funnel opening to the groove exposed for introduction of the liquid deadening agent by the typical drug delivery needle. The curved groove causes the flexible tip of the inserted needle to bend upwards in the groove in such a manner that it first punctures the polyethylene down near the drilling tip and then allows the fluid to be injected into the desired interior region of the jaw.

Although not vital to the design or drug delivery intent of the invention, it should be understood that with careful selection of the polyethylene or other plastic chosen for the covering of the groove, removal of the sterile needle allows the perforated plastic to close back on itself. This effectively stops or reduces the introduction of airborne or waterborne bacteria to the inner tissues while the drill is left in place. The use of a rubbery type carbon compound such as polyethylene is cited because a holistic or shatter proof barrier is desired. This means a rupture of the plastic for passage of the needle tip is facilitated without a detachment of large fragmentary particles of the barrier plastic itself.

DETAILED DESCRIPTION OF DRAWINGS

FIG. 1 is a drawing detailing the preferred embodiment of the invention with a conventional drill bit 1 working in advance of an excavated groove 2 of the neck shaft 3 of the drill bit itself. The neck shaft is surrounded by a thin layer of transparent plastic 4 subject to perforation by a hypodermic needle (not shown) entering a funnel entrance (not shown) through plastic hub 5. Hub 5 has been injection molded to encapsulate the far end of neck shaft 3, and is suitable for attachment to a typical adapter interfacing to a hand held dental drill.

FIG. 2 is a drawing detailing a cross section of the preferred embodiment of the invention. Neck shaft 3 is surrounded by thin plastic 4 and the excavated portion allows a hypodermic needle 8 to pass smoothly down the canyon. As a scale reference, grid 9 spans 1 millimeter, and is divided into two dozen divisions representative of the thickness of plastic 4 which in this embodiment is one twenty-fourth of a millimeter. At this scale needle 8 is a standard 30 gage size which is one third of a millimeter in diameter. Arrow 10 points to a central location of the accompanying drawing to visually coordinate the area of the cross section.

FIG. 3 is a drawing detailing a horizontal cross section of the preferred embodiment of the invention so the nature of the scalloped end of groove 2 is visible. A needle (not shown) entering hub 5 at funnel opening 6 is guided by an alignment portal 7 to shepherd the needle properly down the excavated portion of the drill bit. The outwardly deflected tip pierces the plastic 4 to enable a proper release of the anaesthesia. The relative length of the drill bits in the drawings has been compressed to allow all features to be depicted, and the hashed lines of this drawing are indicative of this.

SUMMARY

The sizes recited in the drawings are not inclusive, as it is apparent smaller or larger drill bits and needle pathways can be engineered as desired. This is feasible because specialty gage needles smaller than the depicted 30 gage are available. The drill bit itself can be considerably reduced to even less than a half of a millimeter, with subsequent increased danger of breakage relative to thicker embodiments.

Variations can be applied to the design of the chosen thickness of plastic sleeves or for appendages such as the hub which would in practice be relatively much larger than depicted in the drawings. The hub itself can be separately manufactured for snap fit or push-on locking assembly to the bare drill bit. The hub is functional by not only allowing the drill bit to be interfaced to the dental handpiece, but also as a guidance portal to ensure the Dentist a wider opening to hit the tiny entrance to the groove or canyon.

The many ways of fitting hubs to adapters or chucks or both is a prior art and not of concern to this paper.

It should be noted that the reducing of the girth of the drill by polishing is a step that could be avoided in some embodiments. Alternative variations would have the groove cut along the drill's shaft and then filled with a gel that hardens sufficient to withstand the entry of the drill through the cortical plate. While in place in the bone, the gel is permeable to the passage of the injection needle carrying the medication, and closes back on itself sufficient to reduce the introduction of bacteria as described.

The term hardened gel is used as an all inclusive term to capture all similar chemical compositions following the intent of the invention.

As a variation of this a very soft gel or dense foam could be used which when in the groove is painted with a layer of fast hardening liquid that dries into a virtual plastic shell. This non-brittle shell would still be vulnerable to the upwards thrusting of the injection needle for medication delivery, and the gel or foam could be admixed with an active antibacterial reagent.

Other variations of this reduction of polishing could entail cutting the groove and only polishing down the exterior edges such that a strip of adhesive plastic in the manner of a bandaid would be run along the length of the groove to seal and isolate the cavitation.

Other manufacturing methods could use a retractable pin to fill the groove while coating or sealing the surface of the groove contiguous with the shaft of the drill. However, this is seen as an expensive step and possibly could defeat a low cost for a related embodiment.

Another variation would employ media removable from the groove after the drilling process. This would involve a method with an extra step for the dentist. The media, although pliant, could be hardened in the groove around a string or tough rope to a length dangling well beyond the length of the drill bit itself. The hub as shown in FIG. 3 could be formed around the media in such a manner that the diameter of alignment portal 7 is greater than the passage diameter of the media. After the drilling is complete and the adapter with the handpiece is removed, the dentist can grasp the dangling end and pull out the inner groove media through funnel opening 6. To delete the extra procedural step, another more expensive variation embodiment would have the adapter attached to the media's end. After drilling the removal of the handpiece and adapter pulls the inner groove media out immediately all in one step. This would provide the desired result.

Cutting the groove and using the drill without sealing or filling with a hardened gel is contemplated by this invention but not encouraged mainly for reasons of hygiene. The bone itself would serve as the second half of the containment for the insertion of the needle.

Although presented as an aid in Dental procedures, the invention can find use in other medical fields employing perforations of bone for humans or other species.

This invention should not be confined to the embodiments described, as many modifications are possible to one skilled in the art. This paper is intended to cover any variations, uses, or adaptations of the invention following the general principles as described and including such departures that come within common practice for this art and fall within the bounds of the claims appended herein.

I claim:

1. A solid drill bit for facilitating the controlled perforation of the cortical area of the jawbone of humans or other species for subsequent injection of fluids, said drill bit comprising two sections of which a first section terminates in a standard tip suitable for the penetration of bone and a second section abutted to or contiguous to said first section, said second section of a passage diameter equal to or less than equal to a passage diameter of said first section, where said second section has an excavated groove for a majority of the length of said second section placed in a linear manner such that said groove runs along the surface of a shank of said second section of said drill bit in a direction away from said contiguous first section, said groove of a size sufficiently small enough relative to said solid drill bit to not impede the success of a drilling operation through living bone and sufficiently large enough relative to said solid drill bit to allow the tip and shank of a hypodermic needle to pass undeterred along said groove while said solid drill bit is in situ in said living bone, said groove of decreasing depth at the end closest to said first section in a scalloped curvature sufficient to turn the tip of said needle in a direction such that said tip of said needle emerges through a roughly circular plane established by the outer circumference of said drill bit in such a manner that a discharge of fluid from said tip of said needle is feasible under operator control, where a distal end of said second section furthest away from said first section is suitable to accept the subsequent fitting of a separate hub designed to allow said groove to continue unimpeded through said hub, where said separate hub is means for further connection to join either with an adapter or with the chuck of a drill.

2. A solid drill bit as in claim 1, further including a contiguous hub designed to allow said groove to continue unimpeded through said hub, where said distal end is manufactured with said contiguous hub attached, where said contiguous hub is means for further connection to join either with an adapter or with the chuck of a drill.

3. A solid drill bit as in claim 1, where the passage diameter of said first section is approximately one millimeter, and said groove of a size to allow at minimum said needle to be a thirty gauge implement.

4. A solid drill bit as in claim 1, with said second section of a passage diameter less than equal to the passage diameter of said first section, further including a thin tubular portion of containment medium a surrounding said second section such that the outside diameter of said surrounded section is of a passage diameter equal to or still less than equal to the passage diameter of said first second section.

5. A solid drill bit as in claim 4, where said containment medium is a rubbery plastic of such pliant composition that said plastic may be penetrated by the sharp tip of a needle without undue force from a dental practitioner, and of such composition that the penetration is holistic and thus without detachment of fragmentary particles of said rubbery plastic.

6. A solid drill bit as in claim 1, wherein a majority of both the surface edges of said groove of said second section is reduced in depth sufficient to allow a strip of containment medium to be adhered to said surface edges in the manner of a adhesive bandage over a wound, such that an upper surface of said strip of containment medium is positioned at a level within a passage diameter equal to or less than equal to the passage diameter of said first section.

7. A solid drill bit as in claim 6, where said containment medium is a rubbery plastic of such pliant composition that said plastic may be penetrated by the sharp tip of a needle without undue force from a dental practitioner, and of such composition that the said penetration is holistic and thus without detachment of fragmentary particles of said plastic.

8. A solid drill bit as in claim 1, wherein said groove of said second section is filled with a hardened gel to a depth maintaining an upper surface of said gel at a level within a passage diameter equal to or less than equal to the passage diameter of said first section.

9. A solid drill bit as in claim 1, wherein said groove of said second section is filled with a pliant gel or dense foam and made sufficiently rigid by painting or coating on an exposed surface of said gel or said foam with a chemical composition having stronger tensile strength relative to said gel or said foam, such that an upper surface of said chemical composition is positioned at a level within a passage diameter equal to or less than equal to the passage diameter of said first section.

10. A solid drill bit as in claim 9, with said pliant gel or dense foam further mixed or compounded with an antibacterial reagent.

11. A solid drill bit as in claim 1, wherein said groove of said second section is filled with a pliant media extending beyond said distal end of said second section furthest away from said first section, said pliant media is of sufficient toughness to allow itself to be grasped by a dentist and withdrawn by force intact from said groove at said distal end after drilling.

12. A solid drill bit as in claim 11, wherein the structural integrity of said pliant media is reinforced with a tough string along the length of said pliant media.

13. A solid drill bit as in claim 11, further including a contiguous hub designed to allow said groove to continue unimpeded through said contiguous hub, where said distal end is manufactured with said contiguous hub attached, where said pliant media within said groove also continues unimpeded through said contiguous hub to a further distance extending beyond a terminating end of said contiguous hub, such that an exposed end of said pliant media at said further distance may be grasped by a dentist and withdrawn by force from said second section through said contiguous hub, where said contiguous hub is means for further connection to join either with an adapter or with the chuck of a drill.

14. A solid drill bit as in claim 13, wherein said exposed end of said pliant media is attached to said adapter or chuck, whereby the removal or detachment of said adapter or chuck from said contiguous hub triggers by force the removal of said pliant media from said groove through said contiguous hub.

15. A method of administering medication through cortical bone, said method comprising the steps of:

deadening the gingiva over said cortical bone;

drilling an opening in said cortical bone with a modified drill bit bearing an excavated groove of longitudinal direction and also bearing a hub suitable for connection to either an adapter or directly to the chuck of a dental drill; said modified drill bit comprising two sections of which a first section terminates in a standard tip suitable for the penetration of bone and a second section abutted to or contiguous to the first section; said second section of a passage diameter equal to or less than equal to a passage diameter of said first section; where a majority of the length of said second section has said excavated groove placed in a linear manner such that said groove runs along the surface of a shank of said second section of said drill bit in a direction away from said contiguous first section; said groove of decreasing depth at the end closest to said first section in a scalloped curvature;

detaching said dental drill from said drill bit and said hub while said drill bit is still penetrating through said cortical bone, inserting the delivery tip and shaft of a hypodermic needle, or a hollow delivery device, down said groove from said hub sufficiently far enough that said delivery tip is deflected by the decreasing depth of said groove and emerges through a roughly circular plane established by the outer circumference of said drill bit;

injecting medication into the desired tissue of the patient;

withdrawing said hypodermic needle or said delivery device and allowing said medication to produce an effect on the patient.

* * * * *